United States Patent
Kodama et al.

(10) Patent No.: US 6,838,685 B1
(45) Date of Patent: Jan. 4, 2005

(54) ION BEAM APPARATUS, ION BEAM PROCESSING METHOD AND SAMPLE HOLDER MEMBER

(75) Inventors: Toshio Kodama, Chiba (JP); Masakatsu Hasuda, Chiba (JP); Toshiaki Fujii, Chiba (JP); Kouji Iwasaki, Chiba (JP); Yasuhiko Sugiyama, Chiba (JP); Yasuyuki Takagi, Chiba (JP)

(73) Assignee: SII Nanotechnology Inc., Chiba (JP)

( * ) Notice: Subject to any disclaimer, the term of this patent is extended or adjusted under 35 U.S.C. 154(b) by 0 days.

(21) Appl. No.: 10/629,217

(22) Filed: Jul. 29, 2003

(30) Foreign Application Priority Data

Jul. 30, 2002 (JP) ........................................ 2002-221929

(51) Int. Cl.⁷ ............................................... H01J 37/26
(52) U.S. Cl. .............................. 250/492.21; 250/442.11
(58) Field of Search ......................... 250/492.21, 442.11

(56) References Cited

U.S. PATENT DOCUMENTS 5,986,264 A * 11/1999 Grunewald ................. 250/310

* cited by examiner

Primary Examiner—Kiet T. Nguyen
(74) Attorney, Agent, or Firm—Adams & Wilks (57) ABSTRACT

An ion beam processing device has a sample holder for fixing a sample on which a section has been formed by irradiation of a specified focused ion beam from a surface side, and gas ion beam irradiation device for irradiating a gas ion beam to a region of the sample fixing using the holder member that contains the section to remove a damage layer on the section. The gas ion beam from the gas ion beam irradiation device irradiates the section from a rear surface side of the sample at a specified incident angle.

17 Claims, 11 Drawing Sheets

ION BEAM APPARATUS, ION BEAM PROCESSING METHOD AND SAMPLE HOLDER MEMBER

BACKGROUND OF THE INVENTION

The present invention relates to an ion beam device and ion beam processing method for carrying out section processing by irradiating an ion beam to a specified part of a sample, and also to a holder member for fixing the sample.

As an ion beam device, a focused ion beam device and an ion milling device are known. These devices are used in sample manufacture when carrying out section observation of fault locations of a wafer using a TEM (Transmission Electron Microscope), for example. In particular, since an FIB device scans a sample surface with a sufficiently focused ion beam and can perform accurate section processing of specific sites such as defects while detecting secondary electrons generated at the time of scanning and observing as an image, FIB devices are widely used as evaluation devices for semiconductor manufacturing processes. Recently, combination type ion beam devices that combine FIB devices and observation devices such as scanning electron microscopes or energy dispersive X-ray detectors, have also been proposed.

Figure 8:
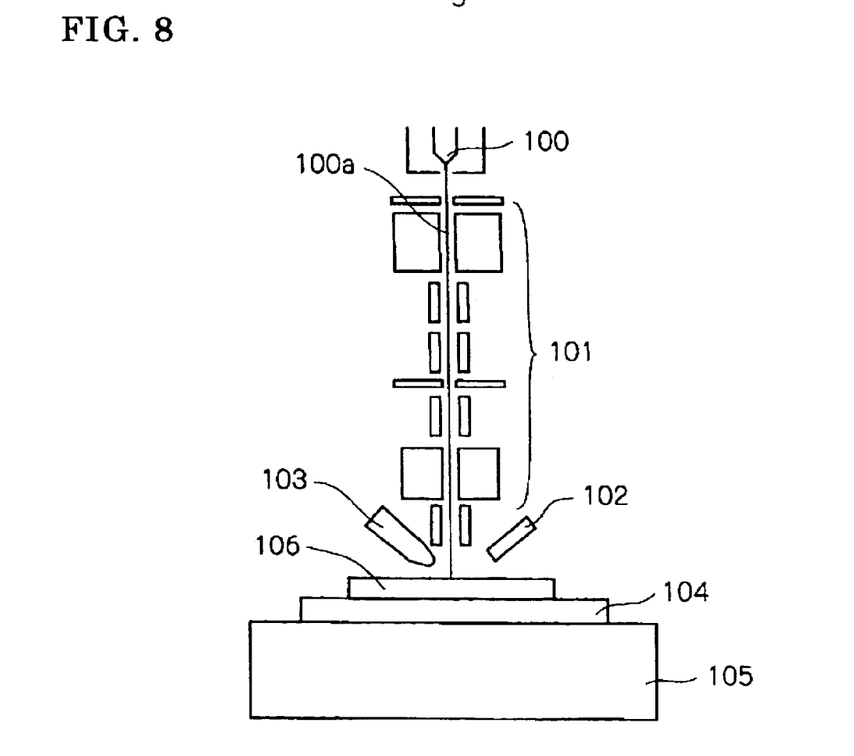
FIG. 8 is a cross sectional drawing schematically showing the structure of a related art FIB device.

The schematic structure of a conventional FIB device is shown in FIG. 8. The main parts of this FIB device are an ion source 100, an ion optical system 101, a secondary charged particle detector 102, a gas gun 103, a sample holder 104 and a sample stage 105.

The ion source 100 is a liquid metal ion source exemplified by Gallium (Ga), for example. The ion optical system 101 is for focusing an ion beam from the ion source 100, as well as scanning the ion beam on the sample 106, and has a condenser lens (electrostatic lens), beam blanker, movable aperture, 8-pole stigmeter, objective lens (electrostatic lens) and scanning electrodes arranged in order from the ion source 100. The secondary charged particle detector 102 detects secondary charge particles generated when the focused ion beam (hereafter referred to simply as FIB) scans the sample 106.

The sample stage 105 can be controlled along five axes. With five axes of control, it is possible to control three dimensional movement in the XYZ directions, rotation around an axis perpendicular to the XY plane, and tilt. The sample holder 104 is for fixing the sample 106, and the sample is conveyed on the sample holder 104 mounted on a moving platform called a boat (not shown in the drawings). The sample 106 is a chip sample subjected to preliminary processing by cutting, for example, defect locations from a wafer using a dicing saw.

Figure 9A:
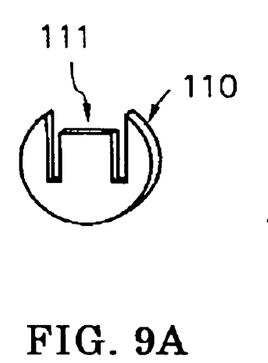
FIG. 9(a) to FIG. 9(d) are perspective views for describing sample holder fixing states being used in the related art FIB devices.
Figure 9B:
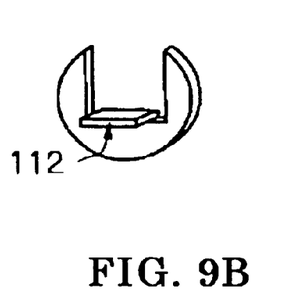
Figure 9C:
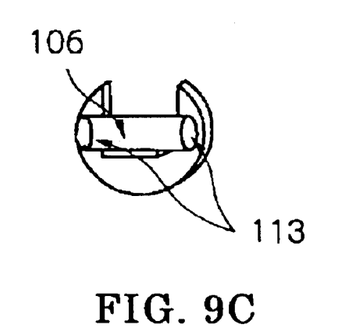

One example of a method of fixing the sample 106 to the sample holder 104 is shown in FIG. 9(a) to FIG. 9(b). A discoid sample holding member 110 that has had a substantially E-shaped part cut out (generally called a mesh) as shown in FIG. 9(a) is prepared, and a step section 112 as shown in FIG. 9(b) is formed by bending a middle part 111 of this sample holding member 110 so as to be substantially perpendicular to the disc surface. Next, as shown in FIG. 9(c), a sample 106 that has been processed into a substantially rectangular block using a dicing saw is mounted on a side surface formed by the step section 112 of the sample holding member 110. At this time, one end surface of the longer edge sides of the sample 106 is in contact with the step section 112. In this state, both ends of the shorter edges of the sample 106 are fixed to the sample holding member 110 using adhesive 113.

Figure 9D:
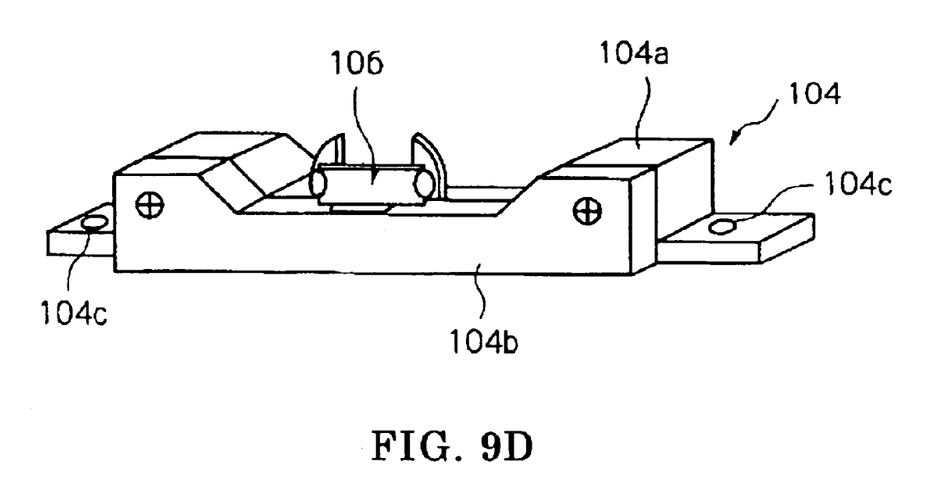

The sample holder 104 comprises a clamp section made up of a receiving section 104a and a press contact section 104b, as shown in FIG. 9(d), and a fixing platform (not shown) to which the clamp section is fixed. A part of the sample holding member 110 that is opposite to a part to which the sample 106 is fixed is clamped by being sandwiched by the receive section 104a and the press contact section 104b. At the time of clamping, by bringing the step section 112 into contact with the upper surface of the press contact section 104b, a clamp position of the sample holding member 110 is regulated. In this manner, the clamp section is fixed to the fixing platform with the sample holding member 110 clamped.

Clamping of the clamp section to the fixing table is carried out by engaging projections (not shown) provided at specified places of the fixing platform into holes 104c respectively provided on both ends of the receiving section 104a, for example. Alternatively, it is also possible for fixing of the clamp section to the fixing platform to have a detachable structure using a latch mechanism.

The sample holder 104 is mounted on a moving table (not shown), and conveyed to the sample stage 105. The fixing platform for the sample holder 104 can also serve as the moving table.

Figure 10A:
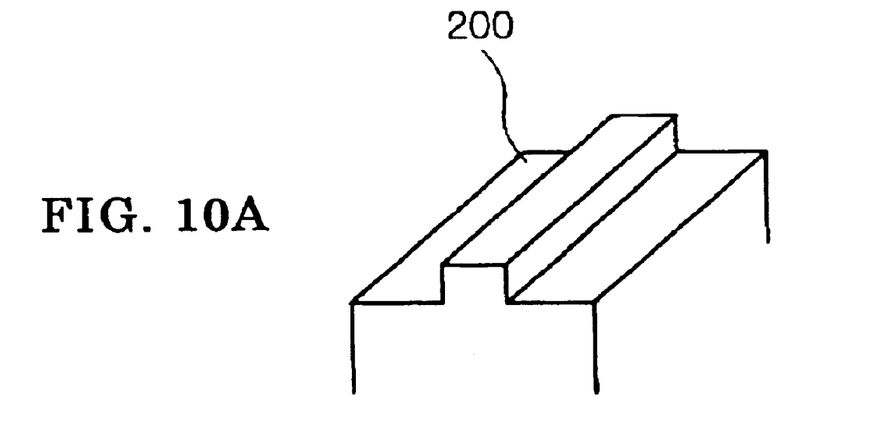
FIG. 10(a) to FIG. 10(c) are process drawings showing a manufacturing sequence for a TEM sample.
Figure 10B:
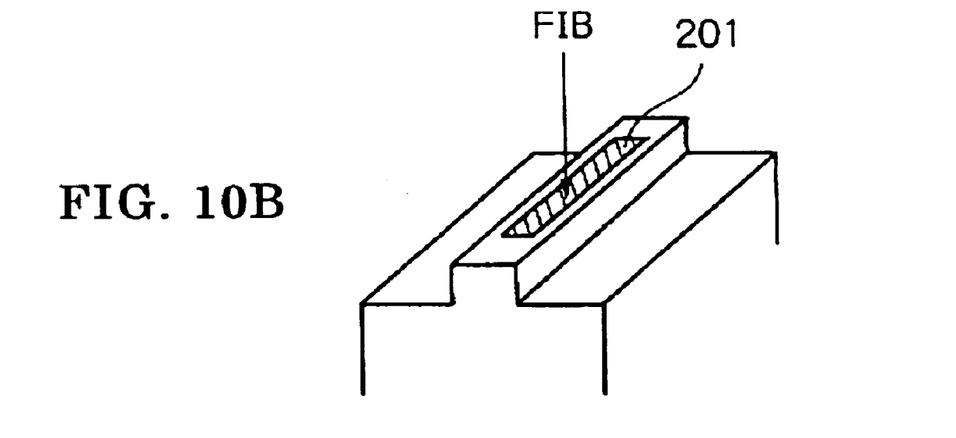
Figure 10C:
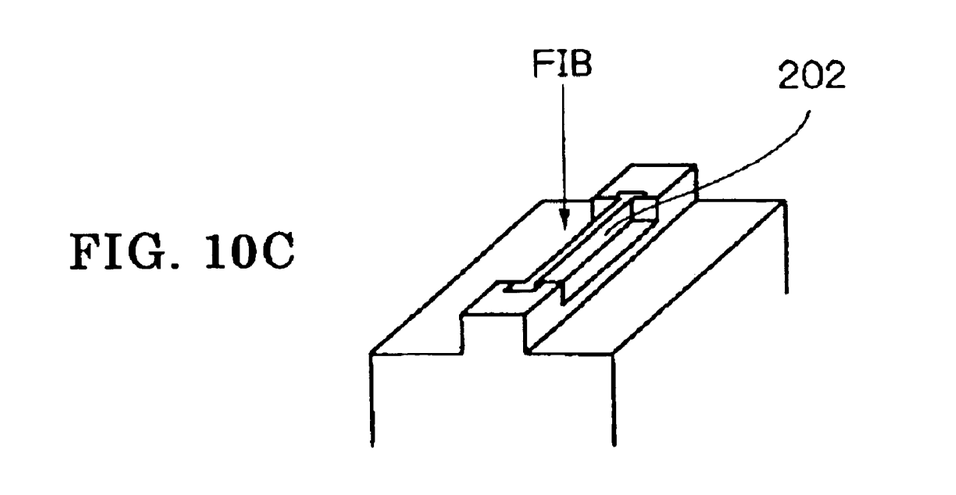

Next, a description will be given of the basic sample manufacturing sequence that uses the above described FIB device. FIG. 10(a) to FIG. 10(c) are process drawings showing a manufacturing sequence for a TEM sample. In the following, the manufacturing sequence for a TEM sample will be described with reference to FIG. 8-FIG. 10.

A defect location of a wafer is subjected to preliminary processing by cutting with a dicing saw, and a convex-shaped sample 200 having a cross section as shown in FIG. 10(a) is formed. The surface of the projecting section of the sample 200 is the surface of the wafer, and in subsequent description the surface of this projection will be made the surface of the sample, while the opposite surface will be made the rear surface of the sample. This sample 200 is clamped to the sample holder 104 by fastening to a sample holder member 110 shown in FIG. 9(d) in a state where the rear surface is in contact with the step section 112. Then, the sample holder 104 is mounted on the moving table (not shown) and conveyed onto the sample stage 105, and position and angle are adjusted on the sample stage 105 so that an FIB from the ion source 100 is irradiated substantially perpendicular to the surface of the sample 200.

Next, specified gas is sprayed onto the surface of the sample 200 using a gas gun 103, and by scanning a range including a region of the surface of the sample 200 to be processed using the FIB from the ion source 100 a protective film 201 as shown in FIG. 10(b) is formed.

Finally, the process region of the surface of the sample 200 is scanned by the FIB from the ion source 100. Since the FIB is irradiated so as to be substantially perpendicular to the surface of the sample 200, the region where the FIB is irradiated has a surface that is gradually shaved off, and finally the cross section 202 shown in FIG. 10(c) is obtained. The cross section 202 shown in FIG. 10(c) is the projection section of the sample 200 shaved away from both sides, and the thickness is from 0.1 to 0.5 $\mu$m. The cross section 202 formed in this way is used as TEM sample.

Figure 11A:
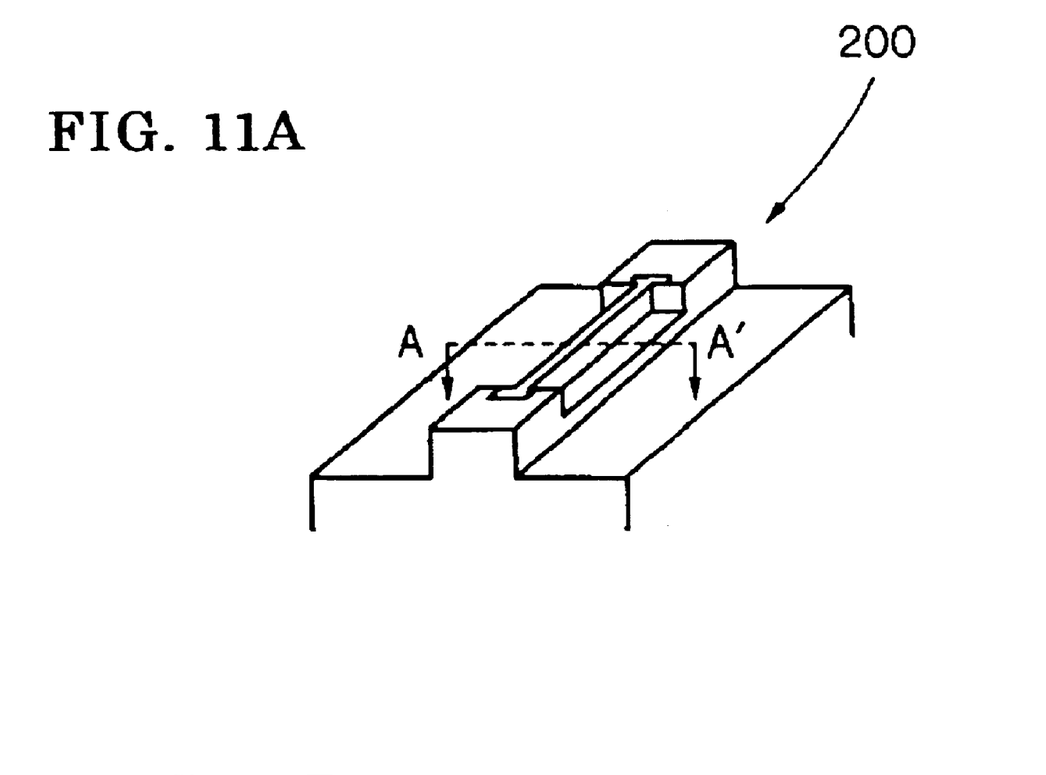
FIG. 11(a) is a perspective view of a TEM sample.
Figure 11B:
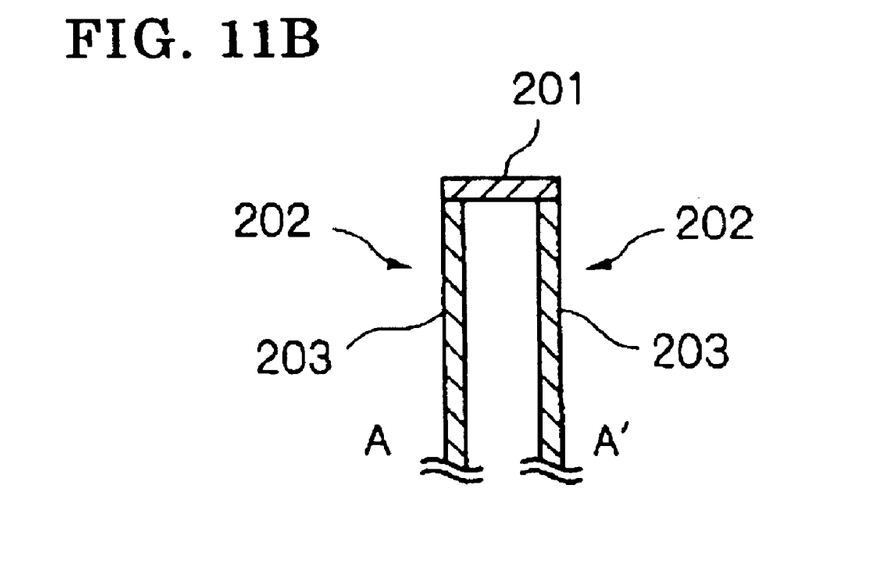
FIG. 11(b) is a cross sectional view taken along line A–A' in FIG. 11(b).

With the above described slicing process, there is damage to the cross section 202 by the FIB. FIG. 11(a) is a perspective view of the TEM sample made with the sequence of FIG. 10(a) to FIG. 10(c) using a Ga ion source as the ion source, and FIG. 11(b) is a cross sectional drawing along line A–A' in FIG. 11(a). In the case of carrying out slicing processing using the FIB from the Ga ion source, the surface of the cross section 202 is subjected to damage by the FIB, and also some of the Ga ions contained in the FIB are injected, to form the damage layer (fracture layer) 203 as shown in FIG. 11(b). The damage layer 203 has an amorphous state with a mixture of elements originally included in the sample itself and injected Ga. If the unwanted damage layer 203 is formed on the surface to be observed in this way, the damage layer proves a hindrance and it is not possible to carry out TEM observation in a satisfactory manner.

A method of removing the damage layer by etching (ion milling) using a low energy ion beam, for example, an argon (Ar) ion beam has been proposed. For example, in Japanese Patent publication No. 3117836 (Japanese Patent Laid-open No. Hei.6-260129), there is disclosed an FIB device capable of removing a damage layer, having a built-in ion milling device.

Figure 12:
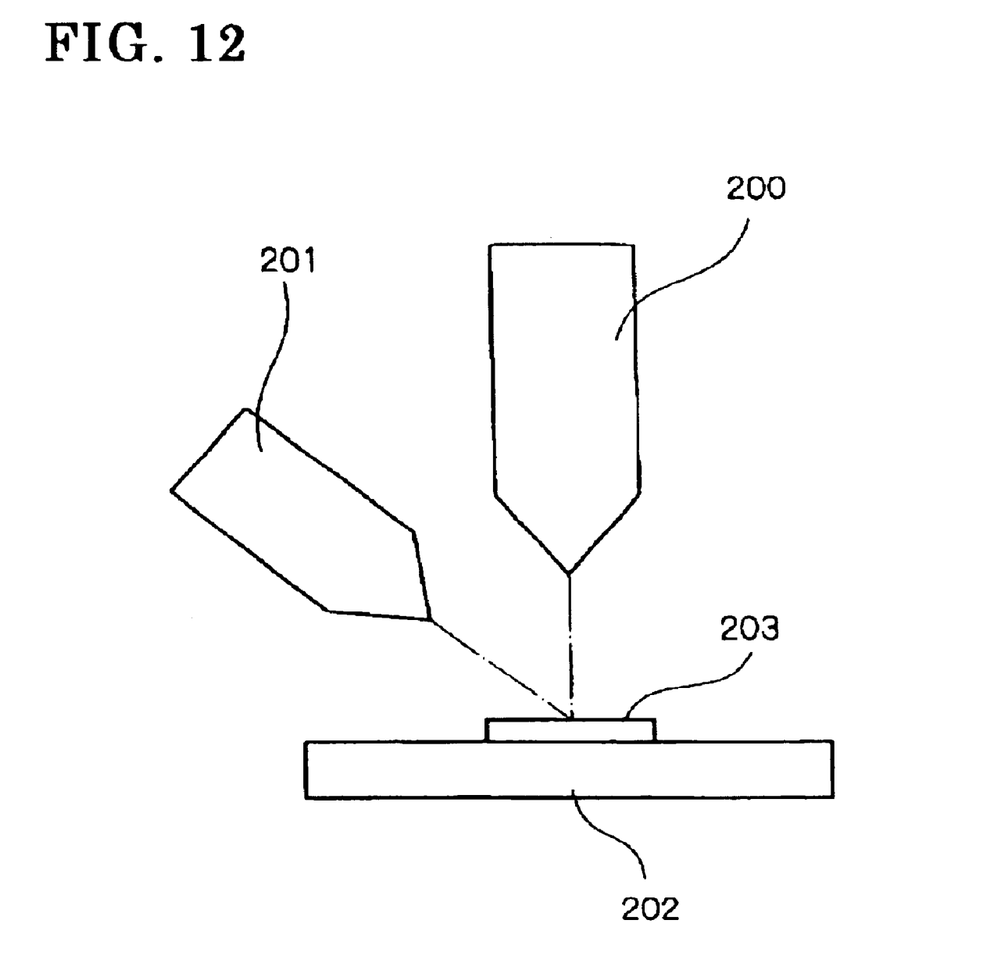
FIG. 12 is a cross sectional view schematically showing the structure of an FIB device disclosed in Japanese Patent Laid-open No. Hei.6-260129.

FIG. 12 is a cross sectional drawing schematically showing the structure of an FIB device disclosed in the above publication. The main elements of this FIB device are a liquid metal ion beam irradiation device (focused ion beam irradiation device) 200, a gas ion beam irradiation device 201, and a sample stage 202.

The liquid metal ion beam irradiation device 200 scans specified parts of the surface of the sample 203 mounted on the sample stage 202 using a sufficiently focused ion beam (FIB) drawn out from a liquid metal ion source. As the liquid metal ion source, there is a Ga ion source, for example. The gas ion beam irradiation device 201 uniformly irradiates a region including a section that has been processed with an ion beam drawn out from a gas ion source.

With the above described FIB device, first of all, the sample 203 is subjected to section processing with an FIB from the liquid metal ion beam irradiation device 200. At the time of this section processing, a damage layer is formed on the section. After section processing, a region containing the processed section is irradiated, and the damage layer on the section is removed by etching.

There is also damage to the section caused by the gas ion beam irradiation, but only to a small extent. The thickness of the damage layer in the case of the liquid metal ion source is 20–30 nm, while for the gas ion beam the thickness of the damage layer is only a few nm, which means that the damage layer does not present a problem in section observation using a TEM or SEM.

As described above, in the case of slicing processing using a FIB, since it is possible to have a damage layer on the processed section, there is a problem in that it is not possible to carry out favorable section observation using a TEM or SEM etc.

By removing the damage layer after section processing with the FIB using the gas ion beam, the above described problem is solved, but in this case, a problem arises with regard to re-attachment of secondary particles, as will be described in the following.

Figure 13A:
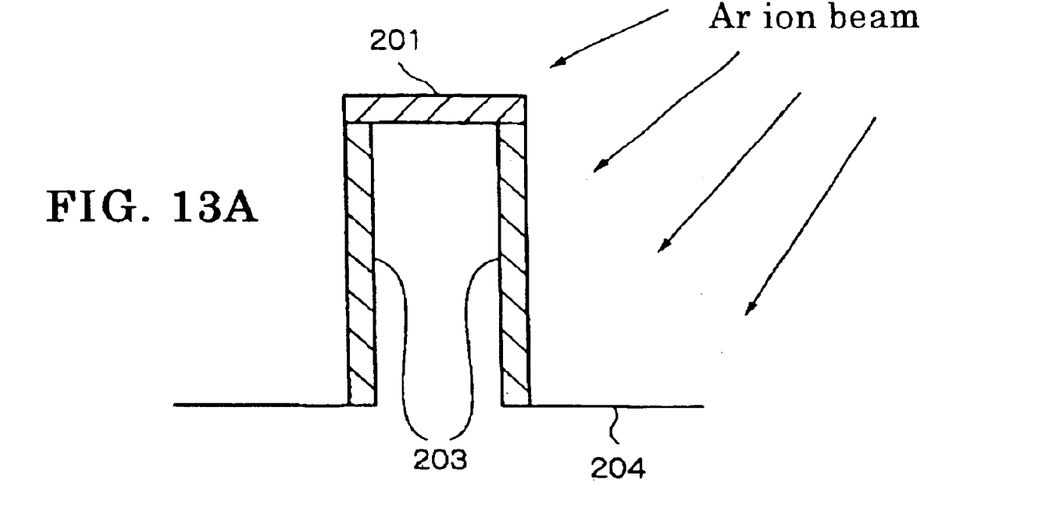
FIG. 13(a) to FIG. 13(c) are schematic diagrams showing stages in formation of a reattachment layer on a cross section.
Figure 13B:
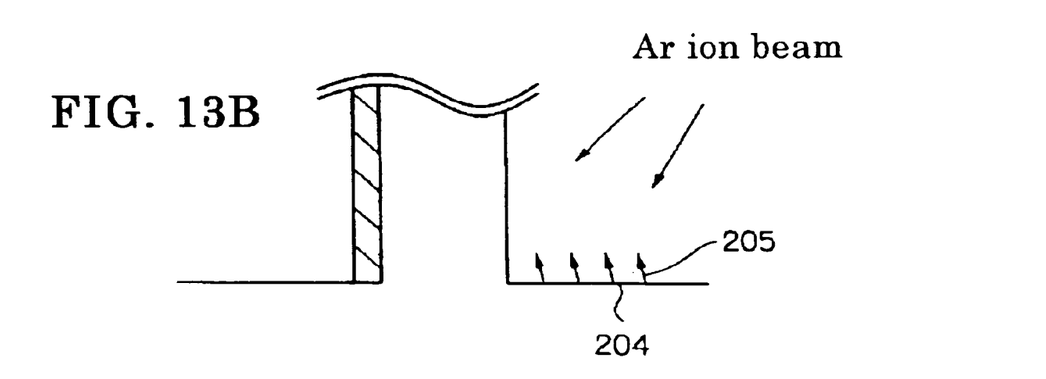
Figure 13C:
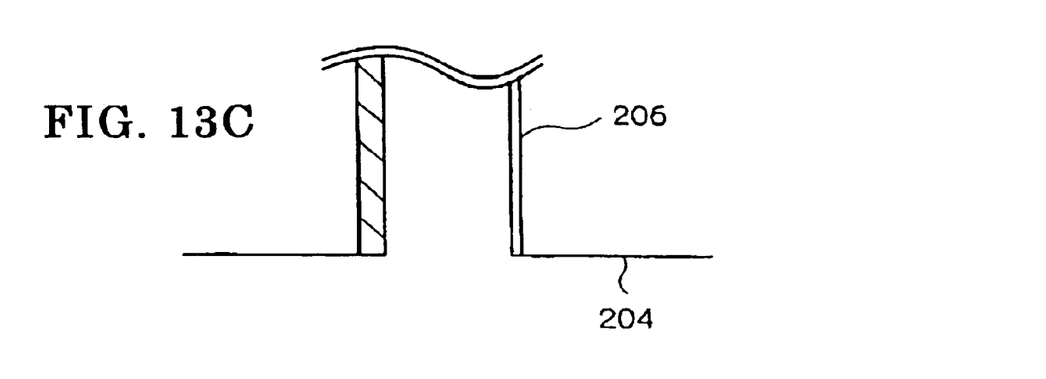

A process of forming a re-attachment layer on the section is shown in FIG. 13(a) to FIG. 13(c). As shown in FIG. 13(a), an Ar ion beam is irradiated in order to remove the damage layer 203 formed on the section. The irradiation range of the Ar ion beam includes an adjacent surface 204 adjoining the section. If the Ar ion beam is irradiated to the adjacent surface 204, then secondary particles are ejected from the adjacent surface 204, as shown in FIG. 13(b). Secondary particles ejected, from this adjacent surface 204 are attached to the section after the damage layer 203 has been removed, forming the re-attachment layer 206 as shown in FIG. 13(c). This re-attachment layer 206 also impedes favorable section observation using a TEM or SEM.

To solve the problem of re-attachment of secondary particles from the adjacent surface due to the Ar ion beam, Japanese Patent Laid-open No. Hei.4-116843 discloses setting the direction of the Ar ion beam so that the Ar ion beam does not irradiate the adjacent surface (this document discloses a bottom surface). However, in this case there is the following problem.

The adjacent surface may also be a surface other than the bottom surface. For example, in the case of a sample that has been subjected to section processing shown in FIG. 10(c), the adjacent surfaces include side walls (side walls formed by the FIB section processing) positioned at both ends of the section 202 in the longitudinal direction, as well as the bottom surface. There is also the above described ejection of secondary particles from these side walls. Since the Ar ion beam is a beam that can not be sufficiently focused, it is not possible to carry out setting so that the two side walls and bottom surface are not irradiated. Accordingly, even if the Ar ion beam direction is set so that the bottom surface is not irradiated, the Ar ion beam will inevitably irradiate the two side surfaces, and a re-attachment layer will be formed on the section.

In addition, in preventing the Ar ion beam from irradiating the bottom surface, the direction and positional relationship of the Ar ion beam with respect to the sample must be set with high precision, and this kind of setting takes time.

By making the region to be processed by the FIB sufficiently large with respect to the diameter of the argon ion beam, it is possible to make the argon ion beam irradiate only the region to be processed, but in this case the processing time using the FIB becomes longer.

The object of the present invention is to solve the above described problems, and to provide an ion beam device, and ion beam processing method, and a holder member, capable of suppressing re-attachment of secondary particles to the section in a straightforward manner.

SUMMARY OF THE INVENTION

In order to achieve the above described object, an ion beam device of the present invention comprises a holder member fixing a sample on which a section has been formed by irradiation of a specified focused ion beam from a surface side, and gas ion beam irradiation means for irradiating a gas ion beam to a region of the sample fixed using the holder member that contains the section to remove a damage layer on the section, wherein the gas ion beam is irradiated from the rear surface side of the sample to the section at a specified incident angle.

According to the above described ion beam device, the following effects are realized.

Since the gas ion beam is irradiated from the rear surface side of the sample, most of the secondary particles go in the direction of the surface side of the sample, and do not go towards the cross section. Therefore, the problem of re-attachment of the secondary particles does not arise.

Also, the gas ion beam can be irradiated at a specified injection angle to a region including a section that has been subjected to section processing, which means that it is not necessary to set the direction and positional relationship of the ion beam with respect to the sample with high accuracy, as with the disclosure of Japanese Patent Laid-open No. Hei.4-116843.

An ion beam processing method of the present invention comprises a first step of forming a section by irradiating a specified focused ion beam from a sample surface side, and a second step of fixing a sample on which the section has been formed from a rear surface side using a holder member, and removing a damage layer on the section by irradiating a gas ion beam to a region including the section from a rear surface side of the sample at a specified incident angle.

In the ion beam processing method also, the same effects are obtained as with the ion beam device described above.

A holder member of the present invention is a holder member for fixing a sample on which a section has been formed through irradiation of a specified focused ion beam from a surface side, and comprises a clamp section for clamping the sample from a rear side thereof, and a fixing platform, provided with a fixing surface arranged so that an angle formed by a gas ion beam irradiated at a specified incident angle with respect to the section becomes equal to the specified incident angle, for fixing the clamp section so that the section of the sample is parallel to the fixing surface.

Also, a holder member of the present invention is a holder member for fixing a sample on which a section has been formed through irradiation of a specified focused ion beam from a surface side, and comprises a clamp section for clamping the sample from a rear side thereof, and a fixing platform, provided with a fixing surface arranged so that an angle formed by a gas ion beam irradiated at a specified incident angle with respect to the section becomes equal to the specified incident angle, for fixing the clamp section so that the section of the sample is perpendicular to the fixing surface, and the surface of the sample is positioned at the fixing surface side.

With any of the above the holder members also, the same effects are obtained as with the ion beam device described above.

In each of the structures of the invention described above, the sample is fixed to a sample holder, described in embodiments later, and includes a sample holding section.

DETAILED DESCRIPTION OF THE INVENTION

Figure 1:
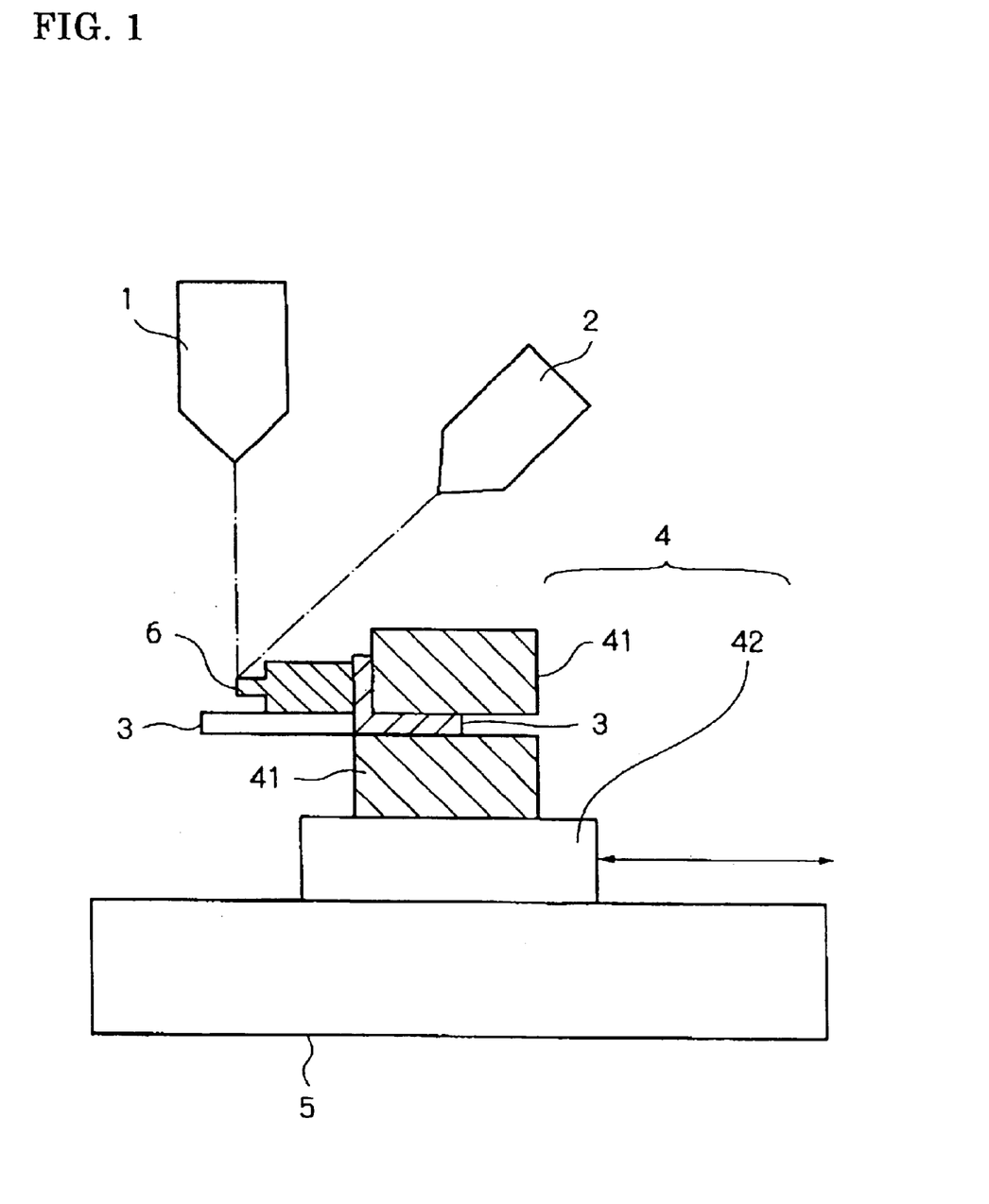
FIG. 1 is a cross sectional drawing schematically showing the structure of an FIB device that is one embodiment of an ion beam device of the present invention.

Next, embodiments of the present invention will be described with reference to the drawings An outline structure of an FIB device, being one embodiment of the ion beam device of the present invention, is shown schematically in FIG. 1. In FIG. 1, the diagonal lines represent a section. The main elements of this FIB device are a liquid metal ion beam irradiation device 1, a gas ion beam irradiation device 2, a sample holding member 3, a sample holder 4, and a sample stage 6.

The liquid metal ion beam irradiation device 1 is a known device for providing a liquid metal ion source, and can carry out processing (section processing) by scanning the surface of a sample with a sufficiently focused ion beam (FIB) drawn out from the liquid metal ion source. A Ga ion source, for example, can be used as the liquid metal ion source.

The gas ion beam irradiation device 2 is a known device for providing a gas ion source, and irradiates a gas ion beam drawn out from gas ion source to a region including a section that has been subjected to section processing using an FIB, at a specified incident angle. A damage layer formed at the time of section processing using the FIB is removed using this gas ion beam irradiation. It is possible to use argon, oxygen, helium, neon, xenon, krypton, radon etc. as the gas.

The optical axis of the gas ion beam irradiated from the gas ion beam irradiation device 2 crosses the optical axis of the FIB irradiated from the liquid metal ion beam irradiation device 1 at a specified position, and an angle formed by the two optical axes is normally set in the range 50°–55°. However, this setting range is merely an example, and it is possible to place in another range.

The sample stage 5 is a known stage capable of control on five axes. The sample holding member 3 is the same as the sample holding member 110 shown in FIG. 9, and fastens the sample 6. The sample 6 is a chip sample that has been subjected to preparation processing by cutting a defect section from a wafer, for example, using a dicing saw, and the sample shown in FIG. 1 is a state before a damage layer is removed, after carrying out section processing using an FIB in the sequence shown in FIG. 10(a) to (c), for example.

The sample holder 4 is made up of a clamp section 41 for clamping the sample holding member 3, and a fixing platform 42 for fixing this clamp section 41. The clamp section 41 is used at the time of removing the damage layer using the gas ion beam, and is fixed to the fixing platform 42 using a detachable mechanism such as, for example, screws or a latch mechanism. The fixing platform 42 has a fixing surface arranged so that an angle formed by the gas ion beam is equal to the specified incident angle, and the clamp section 41 is fixed so that the section of the sample 6 is parallel to the fixing surface. Also, the fixing platform 42 is configured such that at the time of FIB processing, a clamp section for section processing (not shown) is attached instead of the clamp section 41. With this embodiment, the fixing platform 42 also functions as a moving platform for conveying the sample onto the sample stage 5, but it is also possible to provide a moving platform separately from the fixing platform 42.

Figures 2A, 2B:
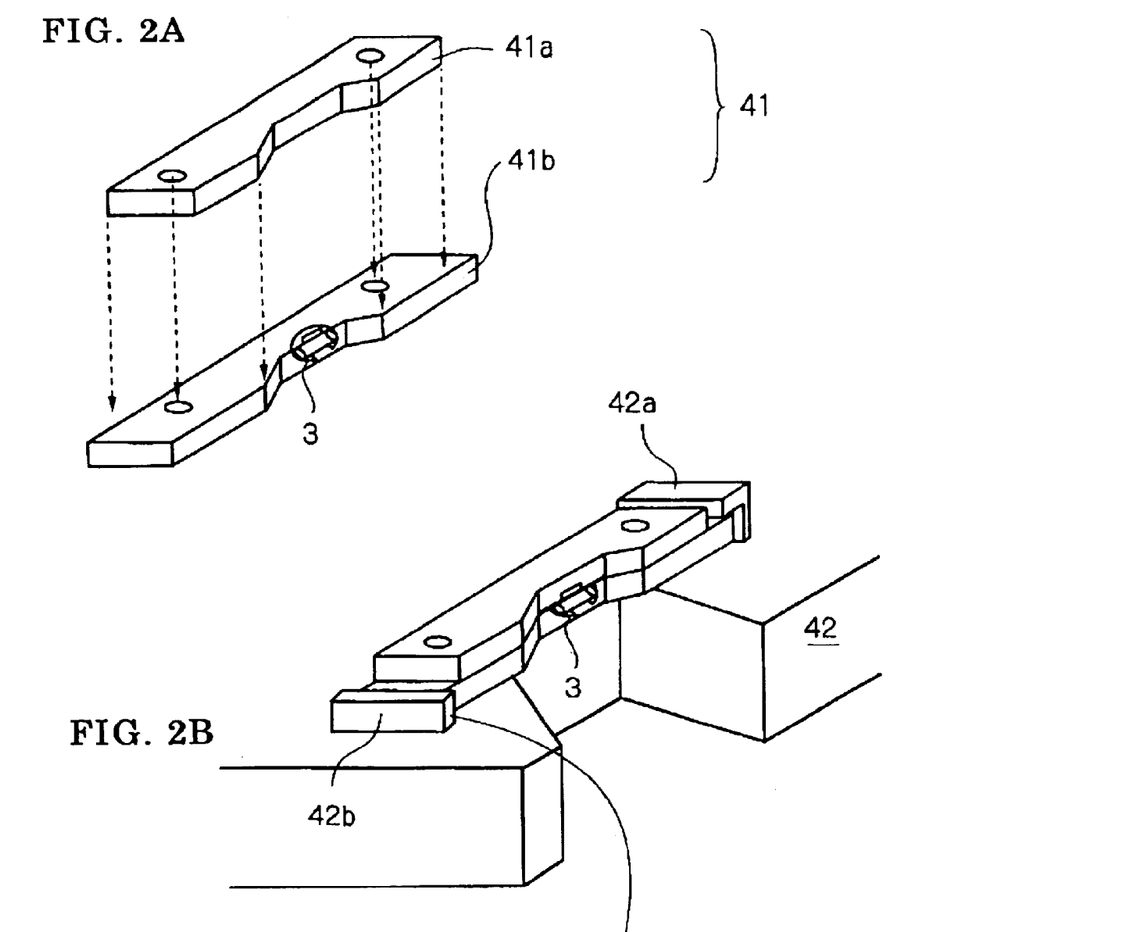
FIG. 2(a) is a partial perspective view of a clamp section of the sample holder of FIG. 1.
FIG. 2(b) is an enlarged perspective view of part of the sample holder of FIG. 1.

One example of the sample holder 4 is shown in FIG. 2. The clamp section 41, as shown in FIG. 2(a), is made up of a press contact section 41a and a receiving section 41b, and the sample holding member 3 holding the sample 6 is clamped by being gripped by the press contact section 41a and the receiving section 41b from a rear surface side of the sample 6. Clamping is carried out by, for example, fixing the clamp section 41 to the receiving section 41b using a screw etc. Positioning of the sample holding member 3 at the time of clamping is carried out using steps similar to the sample holder shown in FIG. 9(d). It is also possible to provide an indentation of a specified size (equivalent to the size of the section of the sample holding member 3 that is clamped) for positioning in the clamp surface of the press contact section 41a or the receiving section 41b, and to have the sample holding member 3 fit into this indentation.

As shown in FIG. 2(b), the fixing platform 42 has an abutment section 42a coming into contact with one end of the clamp section 41, and a fixing section 41b providing a detachable mechanism for fixing the other end of the clamp section 41. The abutment section 42a and the fixing section 42b are arranged facing each other, and the distance between them is substantially the same as the length of the clamp section 41. Also, the fixing platform 42 has a substantially square "c" shaped notch formed in a section where the clamp section 41 is fixed. An end surface of this notch section is at almost the same position as an end surface of a section of the clamp section 41 where the sample holding member 3 is clamped, and the gas ion beam irradiated from the rear surface of the sample passes through this notch and does not irradiate the fixing platform.

Figure 2C:
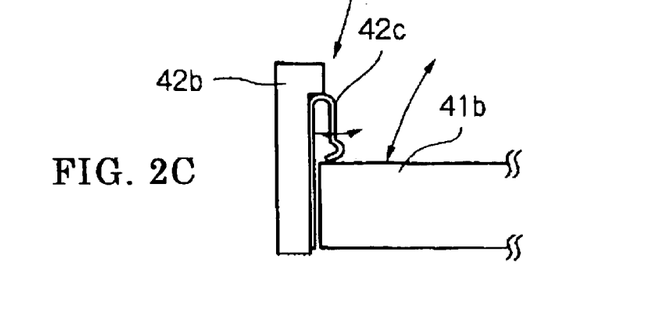
FIG. 2(c) is an enlarged cross sectional view of part of FIG. 2(b).

As shown, for example, in FIG. 2(c), the detachable mechanism is constructed using a plate spring member 42c provided on a surface of the fixing section 42b that contacts the other end of the clamp section 41. In the case where the clamp section 41 is fixed to the fixing platform 42, in a state where one end of the clamp section 41 is in contact with the abutment section 42a, the other end is fixed using the plate spring member 42c by pushing in so as to fit into the fixing section 42. In the case where the clamp section 41 is removed from the fixing platform 42, the other end of the clamp section 41 is held and raised up.

With this embodiment, a clamp section for section processing (not shown) is used separately from the clamp section 41. This clamp section for section processing is similar to the clamp section of the sample holder 104 shown in FIG. 9(d), for example, with the length of the receive section 104a being almost the same as the receive section 41a, and can be fixed to the fixing platform 42. However, in the case of the clamp section for section processing, the rear surface of the sample is arranged so as to be positioned at the fixing surface side of the fixing platform 42. With this type of arrangement, it is possible to carry out section processing by irradiating the FIB from the liquid metal ion beam irradiation device 1 almost perpendicular to the surface of the sample.

Next, the section processing and damage removal method sequence for the FIB device of this embodiment will be described specifically with reference to FIG. 1.

(1) Section Processing

With section processing, the clamp section for section processing is used. The sample holding member 3 holding a sample that has been processed into a block shape by a dicing saw is clamped by the clamp section for section processing, and the clamp section for section processing is fixed to the fixing platform 42. Then, the fixing platform 42 is moved onto the sample stage 5, and the surface of the sample subjected to section processing in the sequence shown in, for example FIG. 10(a) to FIG. 10(c) using the liquid metal ion beam irradiation device 1. This section processing is similar to that of the related art, and forms a damage layer on the section, being the processed surface.

(2) Damage Layer Removal

First of all, the clamp section for section processing is removed from the fixing platform 42, and the sample holding member 3 holding the sample that has been subjected to the section processing described above is taken off from the clamp section for section processing. This removed sample holding member 3 is clamped by the clamp section 41 from the rear surface direction of the sample, as shown in FIG. 2, and the clamp section 41 is fixed to the fixing platform 42. Then, the fixing platform 42 is arranged at a specified position on the sample stage 5, and a region including the section of the sample is similarly irradiated by a gas ion beam from the gas ion beam irradiation device 2 to remove a damage layer. At this time, the gas ion beam is irradiated from a rear surface of the sample 6 at a specified angle of incidence with respect to the section of the sample 6, as shown in FIG. 1, and in this way reattachment of secondary particles is suppressed.

The most characteristic feature of the FIB device of the above described embodiment is, as shown in FIG. 1, the fact that using the clamp section 41 of the sample holder 4, a gas ion beam is irradiated to the section from a rear surface of the sample 6, to suppress reattachment of secondary particles to the section at the time of removing a damage layer.

Figure 3A:
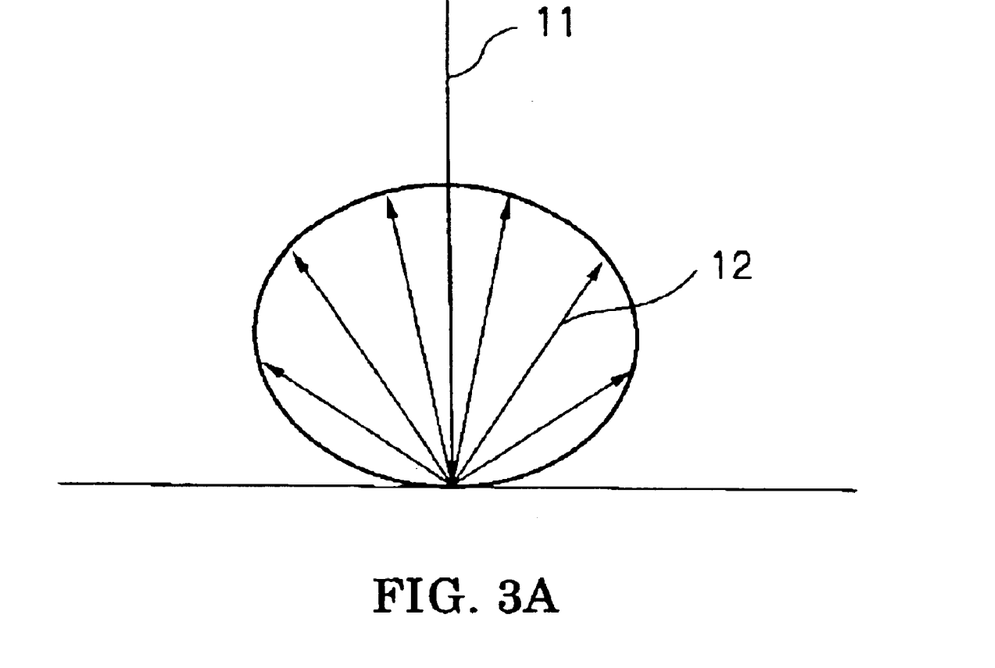
FIG. 3(a) is a schematic drawing showing secondary particle ejection distribution for vertical incidence.
Figure 3B:
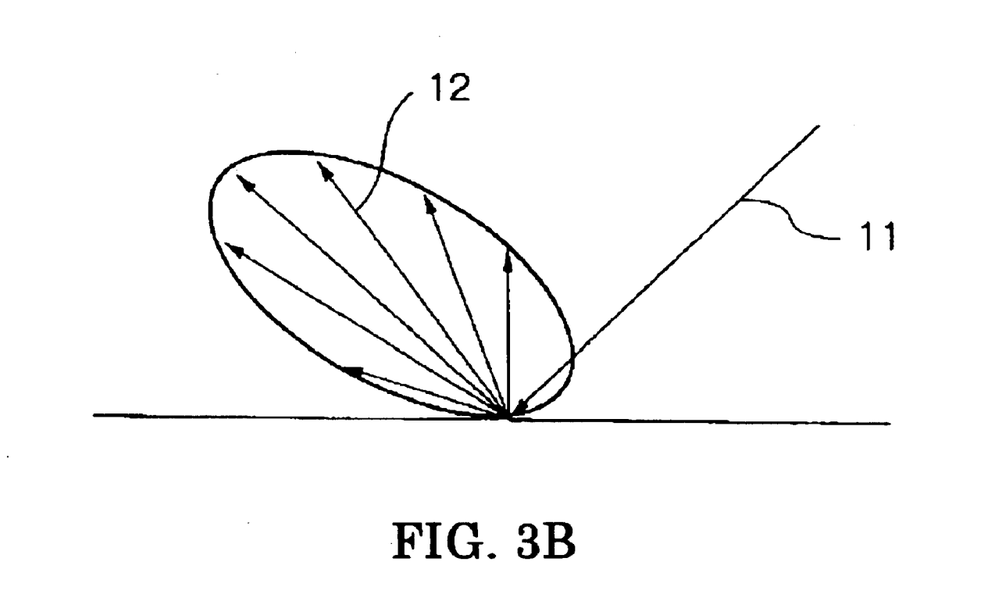
FIG. 3(b) is a schematic drawing showing secondary particle ejection distribution for inclined incidence.

FIG. 3 shows secondary particle ejection distribution. As shown in FIG. 3(a) when the gas ion beam 11 is incident perpendicular to the process surface, secondary particles 12 are ejected radially from the incident point, and this ejection distribution substantially depicts a circle. On the other hand, when the gas ion beam 11 is incident at an incline with respect to the process surface, then as shown in FIG. 3(b) the secondary particles 12 are mainly ejected from the incident point in the opposite direction to the incident direction of the gas ion beam 11, and the ejection distribution is inclined. In this way, it is possible to face the ejection direction of the secondary particles in an arbitrary direction using the incident direction of the gas ion beam.

Also, since section processing of the sample 6 must be carried out by causing an FIB to be incident perpendicular with respect to the surface of the sample 6 to shave off the surface, there is no side wall adjacent to the section at the surface side of the sample 6. There is no side wall irradiated by the gas ion beam at the surface side of the sample 6, and also the sample holding member 3 and the sample holder 4 are not positioned in the advancing direction of the gas ion beam. As a result, by making the gas ion beam from the rear surface side of the sample 6 irradiate the section at an incline, almost all secondary particles ejected from regions other than the section go towards the surface side of the sample 6, and none go towards the section. With the example of FIG. 1, it appears that part of the sample holding member 3 is positioned in the advancing direction of the gas ion beam, but in actual fact, as shown in FIG. 2(b), that section is cut away, and the gas ion beam passes through. The fixing platform 42 is also provided with a cut-away section, and in this way the gas ion beam does not make reach the fixing platform 42.

With this embodiment, based on the above findings, the structure is such that an inclination can be imparted on the secondary particle ejection distribution, and secondary particles ejected from a region other than a section do not go towards the sample. In this way, reattachment of secondary particles on the section at the time of removing a damage layer can be suppressed.

The smaller the incident angle of the gas ion beam on the section the better, but depending on the structure of the sample 6, if the incident angle is made small the gas ion beam may be intercepted by a side wall adjacent to the section, and it will not be possible to irradiate the section. Accordingly, it is necessary to set the incident angle so as to enable irradiation of the section in a certain range. Setting of the incident angle of the gas ion beam with respect to the processing surface in this way makes it possible to carry out control of a tilt angle of the sample stage 5.

In the above description, a sample that has been subjected to processing using a dicing saw is used as the sample 6, but it is also possible to use a sample that has been manufactured using a so-called pick-up method or lift out method, where section processing is carried out by direct irradiation of an FIB to a defect location of a wafer while looking at an image such as an SEM image, and a processed section is cut out. In this case, a sample table is formed in advance on a holding member having the same shape as the sample holding member 3, and the sample is fixed on that sample table.

It is also possible to apply various shapes as the sample holder. In the following modified examples of the sample holder 4 will be described.

(Modified Example 1 of Sample Holder)

Figure 4:
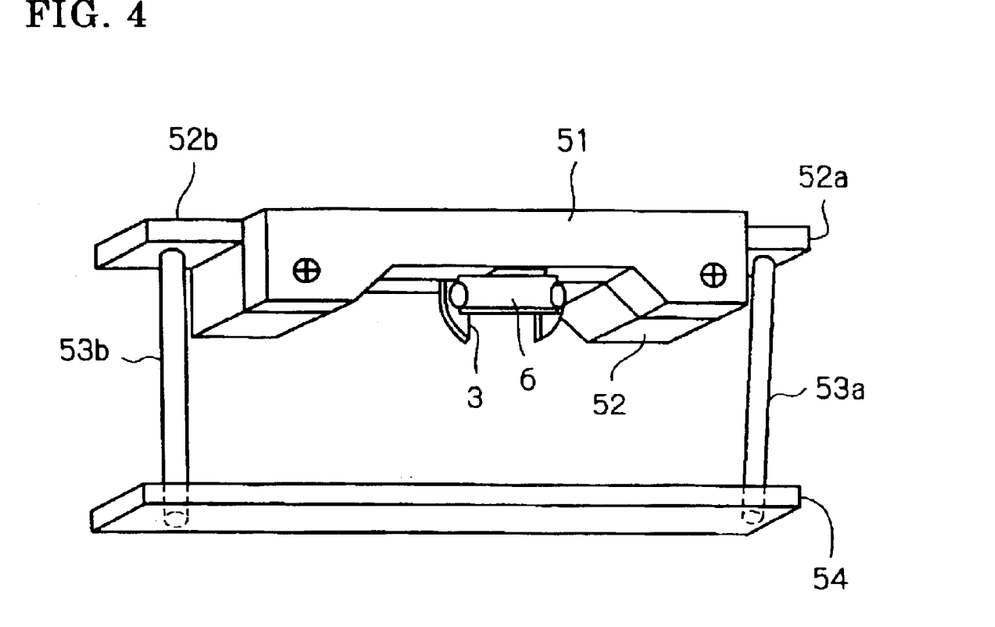
FIG. 4 is a perspective view showing a modified example of part of the clamp section of the sample holder used in the ion beam device of the present invention.

A modified example of a clamp section of the sample holder uses in the ion beam device of the present invention is shown in FIG. 4. This clamp section is made up of a press contact section 51, a receive section 52, support struts 53a and 53b, and a platform 54. The press contact section 51 and the receive section 52 clamp the sample holding member 3. This is almost the same as the structure shown in FIG. 9(d). The two ends 52a and 52b of the receive section 52 are fixed to the platform 54 through the respective support struts 53a and 53b. The platform 54 is fixed to the fixing platform 42 shown in FIG. 2, for example, by bringing one end into contact with an abutment section 42a, and fitting the other end into the fixing section 42b.

The platform 54 is fixed to the fixing platform 42, and a surface of a sample 6 held on the sample holding member 3 is positioned at a fixed surface side of the fixing platform 42. According to this structure, the gas ion beam becomes incident to the section at a specified incident angle from a rear surface side of the sample 6. As a result, with the sample holder of this example also, it is possible to suppress reattachment of secondary particles to the section.

Figure 5:
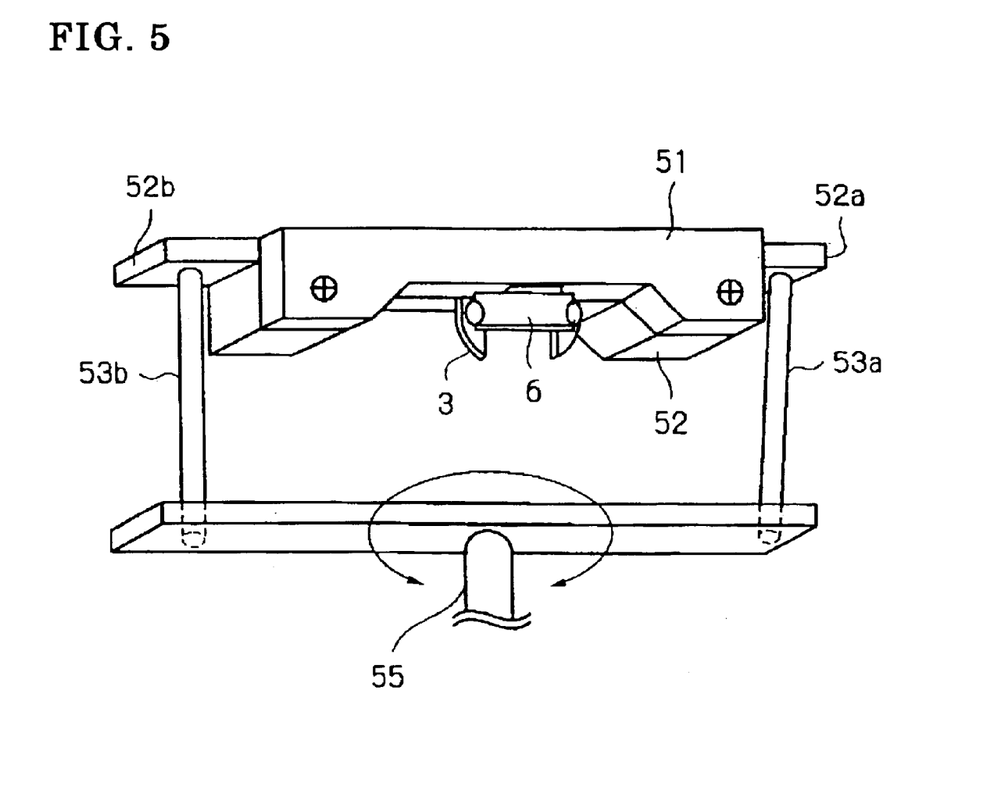
FIG. 5 is a perspective view showing one modified example of the clamp section shown in FIG. 4.

Also, as shown in FIG. 5, it is possible to fix the platform 5 to the fixed side of the fixing platform 42 capable of rotation around a vertical shaft 55. In this case, after removal of a damage layer on one section of the sample stage 6, the platform 54 is rotated by 180° around the shaft 55 and it is possible to remove a damage layer from another section of the sample 6. As a result, it is not necessary to remove the sample, and processing time can be reduced by the amount of time removal would have take, and effort saving can be realized.

In the structure shown in FIG. 5, a small motor for rotating the shaft 55 is provided on the fixing platform 42 side. With the FIB device, in a state where a sample holder is fixed to a sample stage arranged inside a reduced pressure sample chamber, the small motor is controlled from outside the sample chamber. A specific structure achieving this will be described simply below.

Terminals connecting the input lines to the small motor are provided at a specified part of the sample stage (a specified position of the sample holder), and wires taken out from the terminals to the outside of the sample chamber are connected to a drive controller which is external to the sample chamber. In this way, it is possible to control rotation of the sample holder in the drive controller.

Also, the fixing platform 42 may be provided with a small battery as a power supply for the small motor, and a light-receiving section for, if infra-red rays are received, allowing supply of electrical power from the small battery to the small motor while that infra-red light is being received. In this case, infra-ed rays are irradiated to a light receiving section from an infra-red light irradiation device provided outside the sample chamber, and it is possible to control rotation of the sample holder by controlling the irradiation time.

(Modified Example 2 of Sample Holder)

Figure 6:
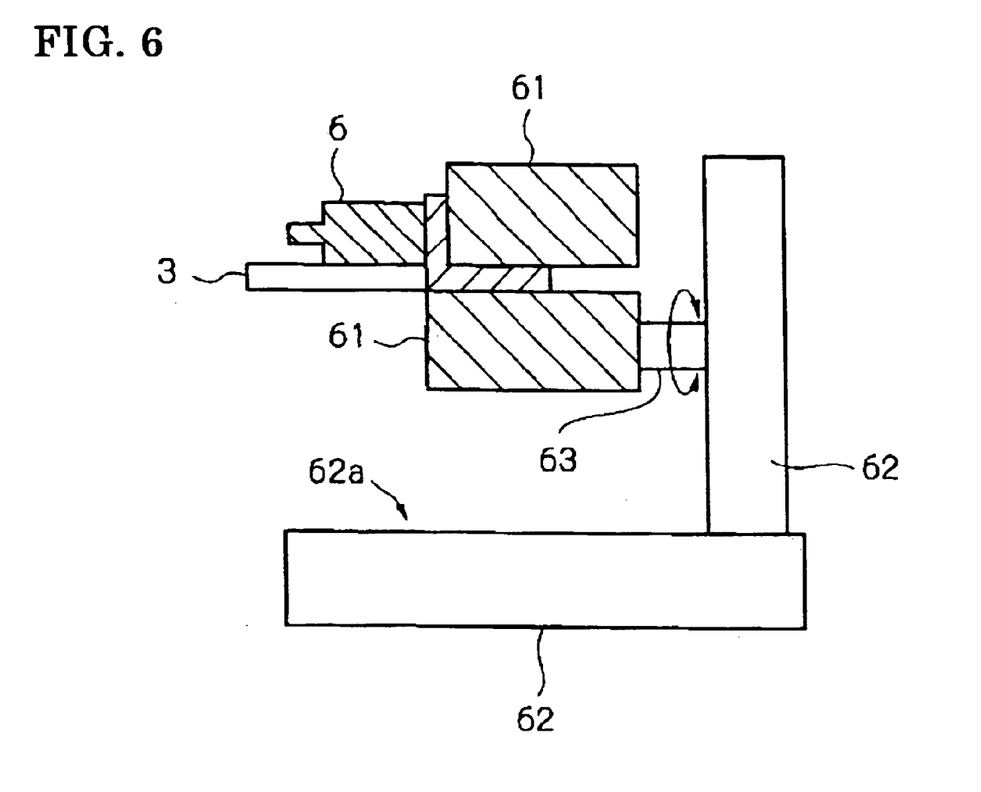
FIG. 6 is a perspective view showing one modified example of a sample holder used in the ion beam device of the present invention.

Another modified example of a sample holder used in the ion beam device of the present invention is shown in FIG. 6. This sample holder has a clamp section 61 for clamping a sample holding member 3 holding a sample 6, and a fixing platform 62 to which the clamp section 61 is fixed.

The fixing platform 62 is provided with a fixed surface 62a arranged so that an angle formed with the gas ion beam irradiated to the section of the sample 6 at a specified incident angle is substantially equal to that specified incident angle. The clamp section 61 is fixed to the fixing platform 62 capable of rotation about a shaft 63 parallel to the fixed surface 62a. According to this structure, after removing a damage layer of one section of the sample 6, it is possible to rotate the clamp section 61 through 180° around the shaft 53 to remove a damage layer of another section of the sample 6. As a result, the sample 6 does not need to be removed, and processing time can be reduced by the time removal would have taken, and effort saving can be realized.

In the FIB device of the above described embodiment, the sample holder can be configured so that a plurality of clamp sections respectively clamping sample holding members are fixed to the fixing platform. In this case, each clamp section is fixed at a predetermined interval, and the position of each clamp section on the sample stage is obtained from a clamp section acting as a datum. With this type of structure, removal of a damage layer using the gas ion beam can be carried out continuously for a plurality of samples, and it is possible to shorten processing time.

Also, at the time of section processing using the FIB and removing a damage layer using the gas ion beam, it is known that stripes occur at the section. For example, in the case of section processing by irradiating an FIB to the surface of a sample having an uneven surface from a direction substantially perpendicular to the surface, the processing rate (etching rate) for boundaries of uneven sections (projections) and flat sections is different, which means that stripes occur corresponding to unevenness of the surface on the formed section. Also in the case where regions (boundaries) of differing properties exist in a section processed region, similar stripes occur. These stripes prove a hindrance to favorable section observation using TEM or SEM.

With this embodiment, by adopting one of either sequence 1 or sequence 2 described in the following, the above described stripes can be removed, and favorable section can be observation realized.

(Sequence 1)

(1-1) Carry out section processing by irradiating the FIB to the sample surface from a first irradiation direction (for example, a direction perpendicular to the sample surface). Stripes will occur at the time of this slicing processing.

(1-2) In order to remove the stripes, irradiate the FIB to the section that has been obtained through the above described section processing from a second irradiation direction that is different to the first irradiation direction. In this way, the stripes formed in the section will be removed.

(1-3) Irradiate a gas ion beam to the section that has had the stripes removed from a third irradiation direction (this irradiation is from the sample rear surface side) to remove a damage layer. With this damage layer removal process, stripes will be formed.

(1-4) In order to remove the stripes formed in the process of step (1-3), irradiate the gas ion beam to the section from a fourth irradiation direction (this irradiation is also from the sample rear surface side) that is different to the third irradiation direction. In this way, the stripes formed in the section will be removed.

The above described step (1-1) and step (1-2) can be carried out at the same time. That is, it is possible to carry out section processing while switching between the first irradiation direction and the second irradiation direction. Similarly, the above described steps (1-3) and (1-4) can also be carried out at the same time. In this case, the damage layer is removed while switching between the third irradiation direction and the fourth irradiation direction.

(Sequence 2)

(2-1) Carry out section processing by irradiating the FIB to the sample surface from a first irradiation direction (for example, a direction perpendicular to the sample surface). Stripes will occur at the time of this slicing processing.

(2-2) Irradiate a gas ion beam to the section that has been obtained through the above described section processing from a second irradiation direction (this irradiation is from the sample rear surface side) that is different to the first irradiation direction, and remove a damage layer on the section. With this damage layer removal process the stripes occurring in step (2-1) will be removed, but new stripes will be formed on the section by the irradiation of the gas ion beam.

(2-3) In order to remove the stripes formed in the process of step (2-2), irradiate the gas ion beam to the section from a third irradiation direction that is different from the second irradiation direction. In this way, the stripes formed in the section will be removed.

The above described steps (2-2) and (2-3) can also be carried out at the same time. That is, the damage layer can be removed while switching between the second irradiation direction and the third irradiation direction. In this case, stripes occurring at the time of section processing and stripes occurring at the time of damage layer removal are removed at the same time.

The switching of the irradiation directions in the above described sequence 1 and sequence 2 is carried out by controlling the tilt angle of the sample stage.

Although an example of an FIB device has been described above, the present invention is not thus limited. For example, it is also possible to have a structure where there is no liquid metal ion beam irradiation device 1, that is a structure where there is only a device for removing a damage layer.

Also, the present invention can be applied to any device as long as it is a device having a mechanism for removing a damage layer on a section formed by FIB processing using a gas ion beam. For example, the structure of the present invention can also be applied to a combined device having an observation device such as an SEM or TEM built in to an FIB device.

Figure 7:
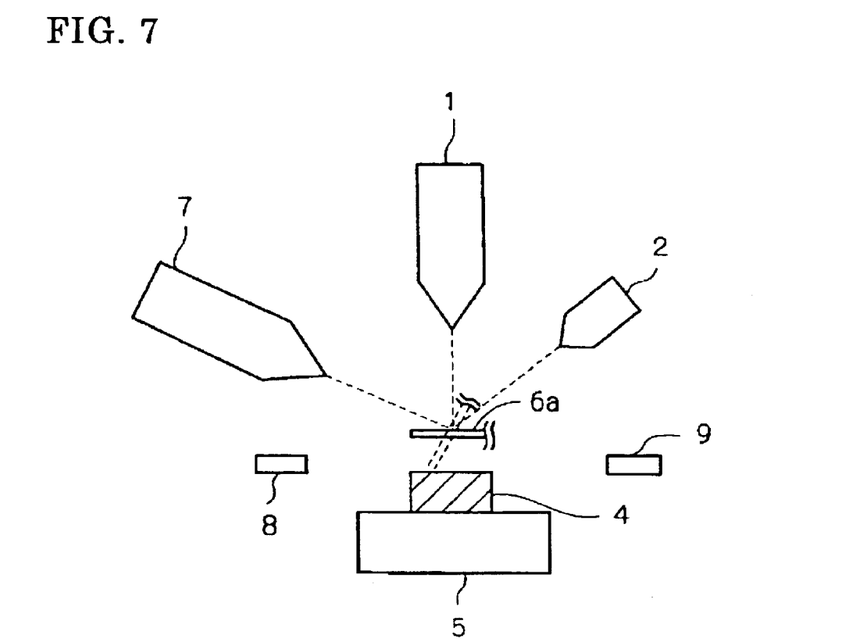
FIG. 7 is a schematic drawing for describing the outline structure of a combined device having functions capable of section observation using an SEM and a TEM built into the FIB device shown in FIG. 1.

The outline structure of a combined device having a function enabling section observation with an SEM or TEM built in to an FIB device is shown in FIG. 7. This combined device is the structure shown in FIG. 1 and is farther provided with an electron beam irradiation device 7 for irradiating am electron beam to a section portion 6a of a sample, as well as a secondary electron detector 8 and a transmitted electron detector 9 for respectively detecting secondary electrons and transmitted electrons from the section portion 6a arising due to irradiation of the electron beam. In FIG. 7, the section shown with the diagonal hatched lines is the sample holder 4 shown in FIG. 1, and the clamp section and the fixing platform have been omitted. The section 6a represents a section portion of the sample 6 shown in FIG. 1.

In the case of carrying out section processing, the clamp section of the sample holder 4 is replaced by the section processing clamp section as shown in FIG. 9(d), and a sample holding member holding the sample is clamped by this section processing clamp section. The surface of the sample is then irradiated with an FIB from the liquid metal ion beam irradiation device 1 to carry out section processing.

In the case of damage layer removal, instead of the section processing clamp section, the clamp section 41 shown in FIG. 1 is used. A sample holding member holding the sample that has had a section formed is removed from the section processing clamp section, and attached to the clamp section 41. Then, the damage layer is removed by irradiating a gas ion beam from the gas ion beam irradiation device 2 from a rear surface side of the section of the sample.

In the case of SEM observation of the section (section portion 6a) that has had the damage layer removed, instead of the clamp section 41, the section processing clamp section is used. A sample holding member holding the sample that has had the damage layer removed is taken off from the clamp section 41, and attached to the section processing clamp section. The tilt angle of the sample stage 5 is controlled so that an electron beam from the electron beam irradiation device 7 is incident perpendicular to the section portion 6a (this is the state of the section portion 6a represented by a dotted line in FIG. 7). Then, the electron beam is irradiated to the section portion 6a, and secondary electrons ejected from the section portion 6a are detected by the secondary electron detector 8. An SEM image is obtained based on the output of the secondary electron detector 8.

In the case of TEM observation of the section (section portion 6a) that has had the damage layer removed also, the electron beam is irradiated from a direction perpendicular to the section portion 6a in a sequence of operations that is similar to the above described case for SEM observation. Transmitted electrons transmitting through the section portion 6a are then detected by the transmitted electron detector

9. A SEM image is obtained based on the output of this transmitted electron detector 9.

In the above described ion beam device of the present invention, the acceleration voltage of the gas ion beam is generally from 10V to 10 kV, but it can be a low voltage to reduce damage. However, with a low acceleration voltage, since the etching rate is slowed down, it is preferable to set the acceleration voltage so as to complete etching in a practical time.

As has been described above, according to the present invention, since re-attachment of secondary particles to a section is suppressed, it is possible to achieve the effect of enabling the manufacture of a sample for which favorable section observation can be carried out using a TEM or SEM.

What is claimed is:

1. An ion beam device comprising:
    a holder member fixing a sample with a section formed thereon by irradiation of a specified focused ion beam from a surface side; and
    gas ion beam irradiation means for irradiating a gas ion beam to a region of the sample fixed using the holder member containing the section to remove a damage layer on the section, wherein
    the gas ion beam is irradiated from the rear surface side of the sample to the section at a specified incident angle.

2. The ion beam device of claim 1, further comprising focused ion beam irradiation means for irradiating the specified focused ion beam.

3. The ion beam device of claim 1, wherein the gas ion beam is an inert gas ion beam.

4. The ion beam device of claim 1, wherein the holder member comprises a clamp section for clamping the sample from a rear side thereof, and a fixing platform, provided with a fixing surface arranged so that an angle formed by the gas ion beam becomes equal to the specified incident angle, for fixing the clamp section so that the section of the sample is parallel to the fixing surface.

5. The ion beam device of claim 4, wherein instead of the clamp section, the fixing platform fixes a processing clamp section in order to process the section using the focused ion beam.

6. The ion beam device of claim 4, wherein the clamp section is fixed to the fixing platform capable of rotation about a shaft parallel to the fixed surface.

7. The ion beam device of claim 1, wherein the holder member comprises a clamp section for clamping the sample from a rear side thereof, and a fixing platform, provided with a fixing surface arranged so that an angle formed by a gas ion beam becomes equal to the specified incident angle, for fixing the clamp section so that the section of the sample is perpendicular to the fixing surface, and the surface of the sample is positioned at the fixing surface side.

8. The ion beam device of claim 7, wherein the clamp section is fixed to the fixing platform capable of rotation about a shaft perpendicular to the fixed surface.

9. An ion beam processing method, comprising:
    a first step of forming a section by irradiating a specified focused ion beam from a sample surface side; and
    a second step of fixing a sample with the section formed thereon from a rear surface side using a holder member, and removing a damage layer on the section by irradiating a gas ion beam to a region including the section from a rear surface side of the sample at a specified incident angle.

10. The ion beam processing method of claim 9, wherein the second step includes a step of varying an incident angle of the gas ion beam to remove the damage layer.

11. The ion beam processing method of claim 9, wherein the first step includes a step of varying the irradiation angle of the specified focused ion beam with respect to the surface of the sample, to form a section.

12. The ion beam processing method of claim 9, wherein the gas ion beam is an inert gas ion beam.

13. A holder member, for fixing a sample having a section formed through irradiation of a specified focused ion beam from a surface side, comprising:
    a clamp section for clamping the sample from a rear surface side of the sample;
    and a fixing platform, provided with a fixing surface arranged so that an angle formed by a gas ion beam irradiated at a specified incident angle with respect to the section becomes equal to the specified incident angle, for fixing the clamp section so that the section of the sample is parallel to the fixing surface.

14. The holder member of claim 13, wherein instead of the clamp section, the fixing platform fixes a processing clamp section in order to process the section using the focused ion beam.

15. The holder member of claim 13, wherein the clamp section is fixed to the fixing platform capable of rotation about a shaft parallel to the fixed surface.

16. A holder member, for fixing a sample having a section formed through irradiation of a specified focused ion beam from a surface side, comprising:
    a clamp section for clamping the sample from a rear surface side of the sample;
    and a fixing platform, provided with a fixing surface arranged so that an angle formed by a gas ion beam irradiated at a specified incident angle with respect to the section becomes equal to the specified incident angle, for fixing the clamp section so that the section of the sample is perpendicular to the fixing surface, and the surface of the sample is positioned at the fixed surface side.

17. The holder member of claim 16, wherein the clamp section is fixed to the fixing platform capable of rotation about a shaft perpendicular to the fixed surface.

* * * * *